United States Patent [19]

Hardy

[11] Patent Number: 4,658,817

[45] Date of Patent: Apr. 21, 1987

[54] METHOD AND APPARATUS FOR TRANSMYOCARDIAL REVASCULARIZATION USING A LASER

[75] Inventor: Roger I. Hardy, Cincinnati, Ohio

[73] Assignee: Children's Hospital Medical Center, Cincinnati, Ohio

[21] Appl. No.: 718,069

[22] Filed: Apr. 1, 1985

[51] Int. Cl.$^4$ .............................................. A61B 17/36
[52] U.S. Cl. ................................. 128/303.1; 128/395; 219/121 LL; 219/121 LK
[58] Field of Search ...................... 128/303.1, 395, 396, 128/397, 398; 219/121 L, 121 LL, 121 LK, 121 LG, 121 LN

[56] References Cited

U.S. PATENT DOCUMENTS

| | | | |
|---|---|---|---|
| 3,087,486 | 4/1963 | Kilpatrick | 128/303.18 X |
| 3,538,919 | 11/1970 | Meyer | 128/398 |
| 3,622,743 | 11/1971 | Muncheryan | 128/303.1 X |
| 3,693,623 | 9/1972 | Harte et al. | 128/303.1 |
| 3,821,510 | 6/1974 | Muncheryan | 128/303.1 X |
| 3,982,541 | 9/1976 | L'Esperance, Jr. | 128/303.1 |
| 4,266,548 | 5/1981 | Davi | 128/303.1 |
| 4,269,174 | 5/1981 | Adair | 128/303.18 X |
| 4,311,138 | 1/1982 | Sugarman | 128/397 X |
| 4,336,809 | 6/1982 | Clark | 128/303.1 X |
| 4,564,011 | 1/1986 | Goldman | 128/303.1 |

OTHER PUBLICATIONS

Mirhoseini; M. et al.: Transventricular Revascularization by Laser, Lasers in Surgery and Medicine, vol. 2:187–198 (1982).
Mirhoseini, M. et al.: Revascularization of the Heart by Laser, Journal of Microsurgery, vol. 2:253–260 (1981).
Mirhoseini, M. et al.: Laser Revascularization of the Heart, Lasers in Medicine and Surgery, vol. 357: 98–103 (1982).
Daniell, J. F. et al.: Carbon Dioxide Laser Laparoscopy: Initial Experience in Experimental Animals and Humans, Obstet Gynecol., vol. 59 (6): 761 (Jun. 1982).

*Primary Examiner*—Carlton R. Croyle
*Assistant Examiner*—Paul F. Neils
*Attorney, Agent, or Firm*—Wood, Herron & Evans

[57] ABSTRACT

A surgical carbon dioxide laser is disclosed which includes a handpiece for directing a laser beam to a desired location. Mounted on the forward end of the handpiece is a hollow needle precisely aligned along the laser path. This permits the laser to be used in surgical applications where the needle perforates a porton of tissue to provide the laser beam direct access to distal tissue. The needle is mounted to the handpiece in a manner which provides for forward and lateral adjustment of the needle relative to the laser beam path which insures co-axiality between the laser beam and the needle lumen. This is crucial for the safe use of the laser. The needle is adjusted such that the focal point of the laser beam is approximately at the tip of the needle. This provides maximum energy at the tip of the needle where it is required. This apparatus is particularly useful in transmyocardial devices utilized to provide ischemic endocardial tissue direct access to blood within the ventricular cavity. The device is inserted within the epicardium of the heart; the laser is then activated to vaporize a channel of tissue through the endocardium. This provides for perforation of the endocardium with minimal damage to the epicardium.

18 Claims, 4 Drawing Figures

METHOD AND APPARATUS FOR TRANSMYOCARDIAL REVASCULARIZATION USING A LASER

BACKGROUND OF THE INVENTION

The laser has developed into a very useful tool in modern surgery. Because of pinpoint accuracy and minimal peripheral thermal damage, the laser has found wide use in many areas of medicine. With the introduction of laser units with 25 to 100 watts power output, the carbon dioxide laser has begun to be used for excision and vaporization of tissue in neurosurgery and plastic surgery as well as gastroenterology, urology, otolaryngology, gynecology and, most recently, in cardiac applications.

Lasers are particularly useful in transmyocardial revascularization. Transmyocardial revascularization is a recently developed method for treating ischemic heart disease. Heart disease is the leading cause of disability and death in all industrialized nations, accounting for nearly twice as many deaths as those resulting from cancer. The majority of these deaths are due to ischemic heart disease, a condition in which the heart muscle or myocardium does not receive an adequate nutritive blood supply. Transmyocardial revascularization is a technique used to supplement the blood supply delivered to the heart by providing the ischemic inner surface (endocardium) direct access to blood within the ventricular chamber. Normally the endocardium does not have direct access to the ventricular chamber and receives its nutritive blood supply entirely from the coronary arteries branching through the heart wall from its outer surface (epicardium).

A carbon dioxide laser has been used in transmyocardial revascularization. In short, the laser was used to vaporize tissue from the epicardium through the endocardium to the ventricular chamber, thereby promoting the ischemic myocardium direct access to blood within the chamber.

Using the above technique creates several problems. The vaporized tissue at the heart's outer surface (epicardium) must be sutured to prevent copious blood loss due to the forceful pumping action of the ventricular cavity. This is time-consuming and clearly dangerous to the patient. Further, the focal point of the laser beam cannot be maintained as it proceeds from the epicardium through the endocardium. If the laser beam is focused at the epicardial surface, it will be unfocused mid-way through the heart wall. An unfocused $CO_2$ laser beam does not precisely vaporize the tissue, but instead merely heats and coagulates the tissue. This does not allow for laser perforation through a thick tissue wall. Prolonged durations of the laser beam are required to penetrate the full thickness of the heart wall. This is especially pertinent to the hypertrophied heart. Prolonged exposure to the high energy of the laser beam exposes peripheral tissue to dangerously excessive thermal damage. Furthermore, controlled perforation in a rapidly beating heart may be impossible with prolonged durations of laser activation. It is also difficult to create a straight channel from the epicardium to the endocardium using the above technique in a beating heart.

Generally a large number of perforations are required. The epicardium must be reperforated for each channel created. But channels within the epicardium are usually inappropriate. In most conditions of ischemic heart disease, it is the endocardium, not the epicardium, which is deprived of a nutritive blood supply. In the above technique, the vaporization of the epicardium is incidental to providing the laser beam access to the endocardial tissue.

Although there are many different types of instruments used to focus a laser for surgical uses to date none of these implements are adaptable for use in transmyocardial revascularization. Many different devices have been used to provide for precise application of a laser beam in surgical applications including the combination of a laser beam with a laparoscope or in combination with an endoscope. These devices focus the laser beam slightly beyond the distal end of the operating channel of either the endoscope or the laparoscope and provide an intense laser beam at a precise location.

Another device used to apply a laser beam to a particular location is described in Davi U.S. Pat. No. 4,266,548. Davi discloses a surgical laser coupled with a hollow canula to direct a laser beam to tissue which is to be vaporized. This apparatus is used in the treatment of cardiac myopathies due to structural and functional abnormalities. In this application an incision is made in the heart to locate the area to be vaporized and provide access to the canula.

Clark U.S. Pat. No. 4,336,809 discloses a xenon ion laser which uses an optical needle to apply laser light to a desired area. The needle has a fiber optic core used to transmit the light to the desired region. Such fiber optic systems are presently incompatible with high intensity infrared lasers such as carbon dioxide lasers. Therefore, it is unsuitable for use when high intensity radiation is required.

SUMMARY OF THE INVENTION

The present invention is premised on the realization that a surgical instrument can be provided which includes a needle which is adapted to be mounted to a laser body with means to align the shaft of the needle along the path of the laser beam. The needle acts to cut or perforate tissue and provide a path for the laser beam.

Further, the invention is premised upon the realization that such a surgical instrument can be provided with means to axially adjust the needle to enable the tip of the needle to be positioned at the focal point of the laser beam. This permits use of different needles having different lengths, yet maintaining the tip of the needle at the focal point of the laser beam.

A preferred embodiment of the invention incorporates a $CO_2$ surgical laser. This instrument can be specially adapted for use in particular operations such as transmyocardial revascularization wherein the shaft of the needle is specially adapted or sized for this end use.

The surgical laser can be provided with an injection port to permit forcing of saline through the needle to clean out the interior of the needle.

The present invention is further premised upon the realization that transmyocardial revascularization can be performed efficiently with minimal damage to the epicardium by focusing a carbon dioxide laser through a short needle, puncturing the epicardium with the needle and subsequently cutting through the endocardium with the laser beam.

The technique of transmyocardial revascularization is significantly improved when aided by the present invention. By initially perforating the epicardium with the laser needle device, the needle's tip is then exposed to the endocardium for lasering and vaporization. The insertion of the device within the epicardium does not vaporize the tissue of the outer heart wall. Instead, it simply separates the tissue which recoils to its native position after the needle's removal. With use of the disclosed apparatus, each of the above cited problems is remedied. There is no vaporization of the heart's outer surface, thereby eliminating surface bleeding and the need for suture. Because the laser beam is focused not at the epicardial surface but at the needle's tip a sharp focus is provided at the endocardium. This invention provides for only vaporization of the endocardium, thereby significantly decreasing the duration of laser activation. Also, placement of the apparatus within the epicardium serves to, in effect, anchor the laser beam. The device moves in accordance with the heartbeat, thereby decreasing peripheral damage. The present invention permits formation of multiple channels within the endocardium with only one needle perforation of the epicardium. Once the apparatus is inserted within the epicardium, multiple pivots of the handpiece at different angles provide multiple endocardial channels. The vaporized channels are appropriately created only within the endocardium.

This invention as well as its advantages will be further appreciated in light of the following detailed description and drawings in which:

DETAILED DESCRIPTION

Figure 1:
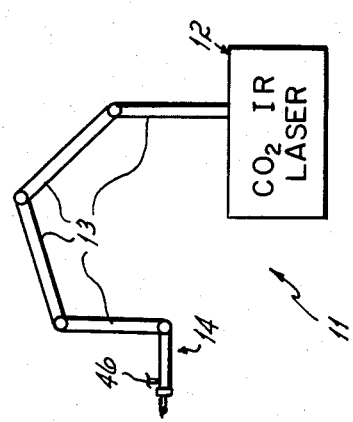
FIG. 1 is a schematic view of a surgical laser system for use with the present invention.
Figure 2:
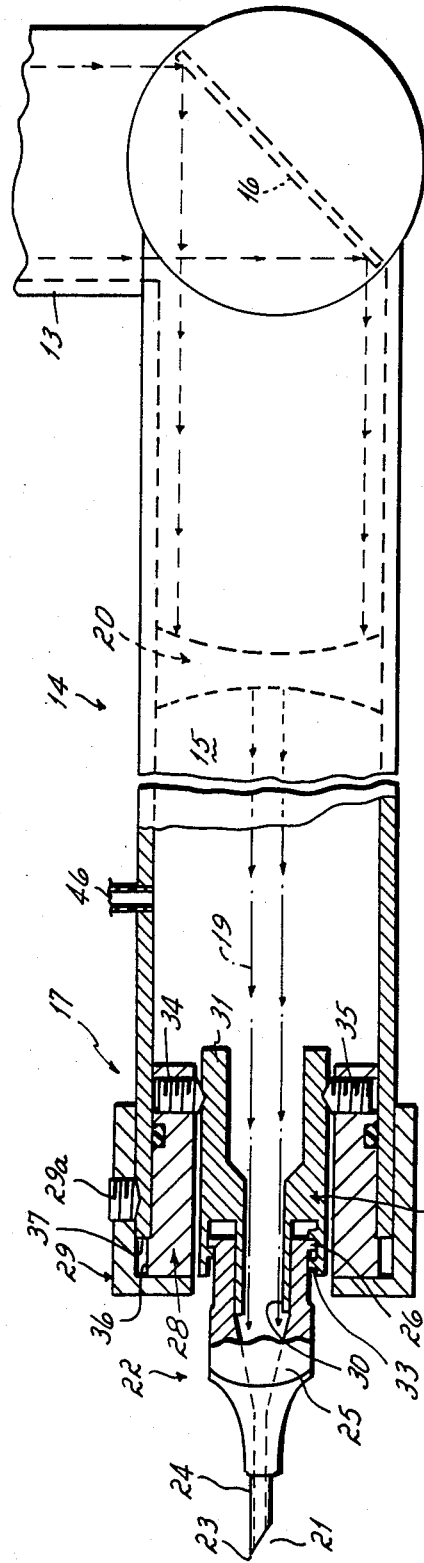
FIG. 2 is a cross-sectional view of the handpiece of the present invention.

As shown in FIG. 1, a surgical laser 11 suitable for use in transmyocardial revascularization includes a source of high energy laser light depicted diagrammatically as 12. Preferably this source of laser light will be a carbon dioxide laser which radiates a beam of high energy laser light through a series of arms 13 to a hand held manipulator or handpiece 14. The arms 13 include a series of mirrors (such as mirror 16, FIG. 2) which direct the generated laser beam to the handpiece 14 and permit relatively free movement of the handpiece independent the carbon dioxide laser 12. A remote foot switch (not shown) is also provided to activate the laser.

The handpiece 14 includes a tubular body 15 which provides a path for a laser beam directed from the mirror 16 to the forward end 17 of body 15. Also within the body 15 is a focusing lens 20 which acts to focus the carbon dioxide laser beam at a fixed focal point 21 forward of forward end 17. The lens directs the laser light reflected from mirror 16 along a laser beam path shown in dotted lines 19. The laser beam reaches its highest intensity at its focal point 21. This focal point is determined by the location and shape of lens 20.

The laser beam path extends through a hollow needle 22. The needle 22 includes a pointed tip 23, shank 24 and an enlarged body portion or hub 25. The hub 25 has flared shoulders 26 which cooperate with external threads 33 of a needle mount or holder 27 to provide a means to attach the needle 22 and hold it stationary with respect to the handpiece. The interior of hub 25 is preferably hollowed out as much as possible to provide clearance for the laser beam.

The needle 22 mounts to the body 15 of handpiece 14 in a manner which enables the location of the needle to be adjusted relative to the body 15 and thus relative to the laser beam path. More specifically, the needle 22 threads into needle mount 27 which is adjustably positioned within a hollow cylindrical holder 28. The holder 28 is fixed to the body 15 by a cap 29.

The needle mount includes a hollow cylindrical metal body 31 and a tubular extension 30 adapted to fit within the hub of needle 22. The externally threaded portion 33 lies between the tubular extension 30 and the body 31.

The needle mount 27 is spaced from the tubular holder 28. This spacing permits the needle mount to be moved forwardly, rearwardly and laterally relative to the holder 28 and thus relative to the handpiece 14 to insure that the laser path extends directly through the needle 22. The exact position of needle mount 27 relative to the holder 28 is fixed by a pair of opposed set screws 34 and 35 which pass through the holder 28 and impinge upon the surface of needle mount 27. Thus these provide for forward, rearward and lateral adjustment of the needle mount and thus needle 22 relative to the body 15.

The holder 28 has a shoulder 36 which abuts the end surface 37 of the body 15 of the handpiece 14. Holder 28 is held in place by cap 29 which can be fixed to the body 15 by various means. As shown in FIG. 1, the cap is held in position by set screw 29a.

The handpiece is also provided with structure which permits the flushing of the needle with saline should it become plugged or fouled. The handpiece includes a port 46 which permits introduction of saline into the handpiece between lens 20 and needle 22. Saline forced into port 46 floods the area between lens 20 and needle 22. The saline is forced through the shank 24 of the needle cleaning the needle.

In operation the laser light generated by the carbon dioxide laser 12 reflects off mirror 16 passes through the handpiece through lens 20 where it is focused at focal point 21. The focal point 21 should lie at the tip of needle 22 or at least within about 3 cm of the tip. Further the laser beam path 19 should pass directly through the hollow interior of the needle. To provide for this the needle is mounted on needle mount 27 and the needle mount 27 is adjusted relative to holder 28 and laser body 15 to align the hollow interior of the needle along the laser path with the tip 23 of the needle at about the focal point 21. The focal point for a laser with a certain lens should be known and thus the position of the needle point adjusted accordingly. The forward and rearward adjustment is made by removing cap 29, loosening the set screws 34 and 35 and moving the needle mount 27 forwardly or rearwardly relative to holder. This adjustment permits needles having various length shanks to be used and interchanged if desired. The lateral adjustment is established by relative movement of the set screws 34 and 35.

This laser can be used in operations in which a laser beam is required at an unexposed portion of an organ. The point of the needle is sharp enough so that as it penetrates tissue it creates an opening by spreading the tissue apart providing a path for the laser beam. This causes only minimal tissue damage. The length of the needle shank is chosen according to the desired depth of this needle puncture and will vary from operation to operation. The gauge of the needle is also a variable according to the size of the generated laser beam. Typically an 18 gauge thin welled needle is suitable, although a different gauge needle may be desired or required with different carbon dioxide lasers.

One particular application for which this apparatus is particularly suited is transmyocardial revascularization. In this application it is desirable to cut holes through the endocardium into one of the heart cavities to allow blood to pass from the cavity into the endocardium. Typically this method will be used to restore blood flow to an ischemic subendocardium perhaps associated with left ventricular hypertrophy. Specifically this provides ventricular blood to the myocardial vasculature.

According to the present invention, transmyocardial revascularization is conducted by surgically exposing the exterior surface of the heart. The left anterior free wall of the left ventricle near the left anterior descending and left circumflex coronaries are subjected to laser treatment. These are the areas which tend to be most ischemic. The ischemic areas are provided with as many perforations as possible without affecting the contractility of the heart. Generally in any area 10 to 20 perforations per square centimeter are created.

Figure 3:
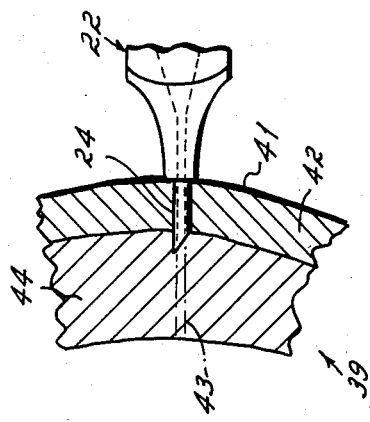
FIG. 3 is a cross-sectional perspective view broken away of the heart undergoing transmyocardial revascularization according to the method of the present invention.

As shown in FIG. 3, to perforate the endocardial tissue of the left anterior free wall of the left ventricle the needle 22 is simply pressed into the epicardial portion 42 of the anterior free wall of the heart 39 until hub 25 abuts against the epicardial surface 41 of the heart. Typically an ischemic heart can have a thickness of approximately 20 millimeters. Preferably the shank of the needle is about 14 millimeters providing a laser induced perforation of about 6 millimeters. Once the needle is forced into the heart the laser is activated for a period of time sufficient to penetrate through the remaining portion of the endocardium into the left ventricle cavity providing a perforation 43 through the endocardium 44. Generally a period of one to two seconds is sufficient with a laser having 80 watts power. The handpiece is then pulled away to pull the needle from the heart. The needle is reinserted at a separate location and the procedure is repeated until the desired density of perforations is obtained.

Figure 4:
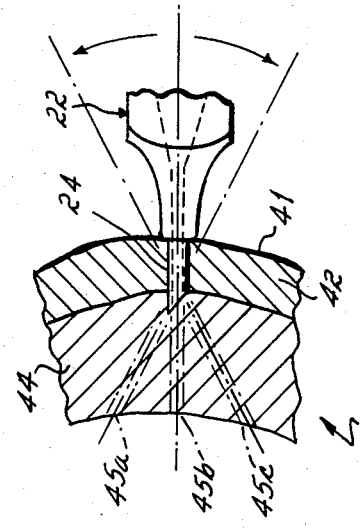
FIG. 4 is a view similar to FIG. 3 illustrating the manner in which the laser may provide multiple perforations.

As shown in FIG. 4 an alternate method of providing multiple perforations is to insert the needle through the epicardium 42 towards the endocardium 44 and provide multiple perforations 45a, 45b and 45c in the endocardium 44. This is accomplished by pushing the needle into the epicardium 42, activating the laser to create first perforation 45a, and subsequently pivoting the handpiece, and again actuating the laser to form second perforation 45b. The handpiece can then be pivoted again about the laser tip and third perforation 45c can be made from the same point but at different angles to provide multiple perforations. This in effect increases the number of perforations through the endocardium without increasing the number of perforations through the epicardium. This reduces the effect this surgical procedure has on the contractility of the heart. These laser induced perforations provide a flow path for blood into the endocardium from the ventricular chamber.

The use of surgical laser of the present invention is not limited to transmyocardial revascularization. Those skilled in the art will readily appreciate the use of the laser in various applications to obtain the benefits of the present invention.

Thus having described my invention I claim:

1. A surgical instrument comprising
a surgical needle having an elongated hollow shaft and an end for cutting through tissue, said shaft adapted for the passage of a lasser beam therethrough, and
means for axially adjusting said needle with respect to a body providing said laser beam to align said needle with said laser beam.

2. The surgical instrument claimed in claim 1 wherein said instrument is adapted for mounting to said body.

3. The surgical instrument claimed in claim 2 further comprising means to adjust said needle axially to position said end of said needle at about a focal point of said laser beam.

4. A surgical laser instrument comprising
a laser body establishing a path for the passage of a laser beam therethrough,
a surgical needle having an end for cutting through tissue and an elongated hollow shaft,
means for mounting said needle with respect to said body, and
means for axially adjusting said hollow shaft with respect to the path of said laser beam to align said shaft with said laser beam.

5. The surgical instrument claimed in claim 4 further comprising means to adjust said hollow shaft axially relative to said laser body to position said end of the needle at about a focal point of said laser beam, said focal point established by said laser body.

6. The instrument claimed in claim 5 further comprising a $CO_2$ laser source adapted to generate said laser beam.

7. The instrument claimed in claim 5 wherein said instrument is adapted for use in transmyocardial revascularization.

8. The instrument claimed in claim 5 wherein said laser body includes a port adapted to permit introduction of a washing fluid into said body thereby permitting the shaft of said needle to be flushed with said washing solution.

9. A surgical laser instrument comprising:
a laser body having a path for the passage of a laser beam therethrough,
a surgical needle having an end for cutting through tissue and an elongated hollow shaft for passage of the beam, and
means to mount said needle to said body comprising a cap fixed to said body, said cap including means to adjust said needle axially and laterally relative to said body for focusing the laser beam at the end of said needle.

10. The apparatus claimed in claim 9 wherein said cap includes a cylindrical holder and a needle mount positioned axially within said holder and fixed in place by at least one set screw extending through said holder against said needle mount.

11. A method of cutting tissue comprising
cutting through a first portion of said tissue by introducing a hollow pointed needle through said tissue,
focusing a laser beam through said hollow needle, and
further cutting through a second portion of said tissue with said laser beam to form a first perforation wherein said tissue is heart tissue and said first portion of said tissue comprises epicardial tissue and said second portion of said tissue comprises endocardial tissue.

12. The method in claim 11 further comprising pivoting said needle and subsequently focusing said laser through said needle to form a second perforation.

13. The method claimed in claim 11 further comprising establishing a focal point of said laser beam at about the tip of said needle.

14. The method claimed in claim 13 wherein said laser is a $CO_2$ laser.

15. A method of transmyocardial revascularization comprising
inserting a hollow needle into the epicardium of a heart,
focusing a laser through said needle, and
cutting a perforation through the endocardium into the ventricular chamber of said heart, thereby providing a channel from said ventricular chamber into said endocardium.

16. The method claimed in claim 14 wherein said laser is a $CO_2$ laser.

17. The method claimed in claim 15 further comprising pivoting said needle and subsequently focusing said laser through said needle to provide a second perforation through said endocardium.

18. A method of cutting tissue comprising:
cutting through a first portion of said tissue by introducing a hollow pointed needle through said tissue;
focusing a laser beam through said hollow needle;
further cutting through a second portion of said tissue with said laser beam to form a first perforation;
and pivoting said needle and subsequently focusing said laser beam through said needle to form a second perforation.

* * * * *